(12) United States Patent
Schein, Jr.

(10) Patent No.: US 9,678,041 B2
(45) Date of Patent: Jun. 13, 2017

(54) NON-DESTRUCTIVE REAL-TIME MAGNETIC FLUX LEAKAGE IMAGING SYSTEM AND METHOD

(71) Applicant: Steven A. Schein, Jr., Tallahassee, FL (US)

(72) Inventor: Steven A. Schein, Jr., Tallahassee, FL (US)

(73) Assignee: City of Tallahassee, Tallahassee, FL (US)

(*) Notice: Subject to any disclaimer, the term of this patent is extended or adjusted under 35 U.S.C. 154(b) by 26 days.

(21) Appl. No.: 14/809,101

(22) Filed: Jul. 24, 2015

(65) Prior Publication Data

US 2016/0025680 A1     Jan. 28, 2016

Related U.S. Application Data

(60) Provisional application No. 62/028,366, filed on Jul. 24, 2014.

(51) Int. Cl.
*G01R 33/00* (2006.01)
*G01N 27/82* (2006.01)

(52) U.S. Cl.
CPC .................................. *G01N 27/82* (2013.01)

(58) Field of Classification Search
CPC .... G01R 33/12; G01R 33/1269; G01R 27/04; G01L 3/101; G01N 27/82; G01N 17/04; H01L 29/045; H01L 39/126
USPC ........ 324/228–234, 200, 210, 213, 451–467, 324/263, 600, 663, 717, 500, 529, 750.12, 324/750.21, 754.17, 754.29
See application file for complete search history.

(56) References Cited

U.S. PATENT DOCUMENTS

| 4,789,827 A | 12/1988 | Bergander |
| 6,023,986 A | 2/2000 | Smith |
| 8,629,572 B1* | 1/2014 | Phillips ................... F03B 13/16 290/42 |
| 2012/0109565 A1 | 5/2012 | Tsukada |
| 2013/0147471 A1* | 6/2013 | Weischedel ............ G01N 27/83 324/238 |

* cited by examiner

*Primary Examiner* — Melissa Koval
*Assistant Examiner* — Trung Nguyen
(74) *Attorney, Agent, or Firm* — J. Wiley Horton

(57) ABSTRACT

A system and method for acquiring three-dimensional images of a magnetic flux leakage present in steel tendons, which are embedded in concrete and/or grout. The inventive method magnetizes the steel tendon. Transducers detect the intensity of the magnetic field along the steel tendon. Using this magnetic intensity, three dimensional images of the magnetic flux leakage are generated using a data acquisition and computing device.

20 Claims, 13 Drawing Sheets

NON-DESTRUCTIVE REAL-TIME MAGNETIC FLUX LEAKAGE IMAGING SYSTEM AND METHOD

CROSS-REFERENCES TO RELATED APPLICATIONS

This non-provisional patent application claims the benefit of an earlier-filed provisional patent application. The provisional application was assigned Ser. No. 62/028,366. It was filed on Jul. 24, 2014.

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of magnetic imaging. More specifically, the present invention comprises a system used to capture images of the magnetic flux leakage of faults located on steel reinforcing tendons embedded in concrete or grout.

2. Description of Related Art

Bridges and other structures are supported using long, embedded steel tendons. Typically, a steel reinforcing tendon is embedded in concrete or grout in order to account for the lack of tensile strength of a concrete. Often, these steel tendons are damaged. However, since the steel tendons are embedded in concrete or grout, the fault is typically difficult to locate and evaluate. The damage can be caused by human sources or corrosion. In order to decide whether replacement is necessary, the cause of damage must be determined. This can be done by destroying the concrete or grout surrounding the steel tendon or by a non-destructive imaging method. Typically, if the cause of the fault on the tendon is manmade, then replacement is not necessary. However, if the cause of the fault is corrosion, then the tendon is typically addressed or replaced. This is because corrosion is progressive in nature, whereas a cut or hole caused by a worker is not progressive.

Destroying the grout and/or concrete surrounding a steel tendon for inspection is time-consuming, potentially dangerous, and expensive. This method of inspection is not plausible for periodic maintenance of steel tendons. A non-destructive method for inspection greatly reduces time and cost of maintenance. In addition, a destructive method of inspection may jeopardize the integrity of the supporting column, and possibly the entire structure in which it supports.

Thus, the need for a non-destructive method for imaging steel reinforcing tendons has been recognized. It is critical for the safety of the public to have the capability to evaluate the state of a steel reinforcement tendon embedded in concrete or grout. In addition, it is important to decipher the cause of the fault in the tendon. If the cause of the fault is not established, workers may destroy a column for a non-progressive fault, such as a nick or a cut. Since it is not necessary to replace a tendon for a manmade nick, cut or hole, this would be an extreme waste of resources. Thus, using a destructive method of inspection is an extremely costly method of evaluating the state of a steel tendon.

There are methods of inspection used to evaluate the steel tendons embedded in grout or concrete in the prior art that are non-destructive. However, these methods have a number of drawbacks. First, the prior art methods are limited in the data acquired. Second, those methods require significant time and expertise to setup and interpret the data acquired. Finally, the cost to setup and extract useful information from that data acquired from the prior art methods is expensive. The present invention solves these and other problems, as will be described more particularly in the following text.

BRIEF SUMMARY OF THE INVENTION

The present invention comprises a system and method for acquiring three-dimensional images of a magnetic flux leakage present in steel tendons, which are embedded in concrete and/or grout. In order to create the magnetic flux leakage in the steel tendon, the inventive method preferably magnetizes the steel tendon. Once the steel tendon is magnetized, transducers detect the intensity of the magnetic field along the steel tendon. This intensity is preferably proportional to a voltage created by the transducer. Using this voltage, three dimensional images of the magnetic flux leakage are generated using a data acquisition and computing device. Based on these images, a user can determine whether there is a fault in the steel tendon at that location. In addition, the three-dimensional images indicate what type of fault is present in the steel tendon, and therefore whether it should be investigated via a more intrusive procedure.

The present inventive method is preferably non-destructive and non-intrusive with the capability of capturing images of steel tendons through concrete, grout and plastic ducting. By determining the location and source (manmade or corrosive) of a fault in an embedded steel tendon using the current method, one can determine whether a more extreme measure is necessary to evaluate, repair, or replace the steel tendon. Typically, manmade faults do not require further action because of the non-progressive nature of cuts, nicks, and holes. However, corrosion is progressive and requires further investigation of the problem area.

The magnetic imaging device is capable of traversing the length of the tendon. As the invention moves along the tendon, images are generated. This allows the user to determine the location and source of a defect in real-time. Thus, the state of the steel tendon is determined in a quick and efficient manner using simple and quick analysis.

REFERENCE NUMERALS IN THE DRAWINGS

- 10 magnetic flux leakage imaging system
- 12 magnet assembly
- 14 imaging array
- 16 mild steel bar
- 18 tendon tube
- 20 north pole magnet assembly
- 22 south pole magnet assembly
- 24 magnet security device
- 26 central testing cavity
- 28 magnet
- 30 Hall Effect circuit board
- 32 Hall Effect sensor
- 34 magnetic field
- 36 computing device
- 38 data acquisition device
- 40 amplifier
- 42 filter
- 44 A/D converter
- 46 central processing unit
- 48 database
- 50 random-access memory
- 52 south pole magnetic axis
- 54 north pole magnetic axis
- 56 tendon
- 58 twisted steel cable
- 60 plastic conduit
- 61 fault
- 62 housing
- 64 first section
- 66 second section
- 68 handle
- 70 hinge mechanism
- 72 locking mechanism
- 74 tendon opening
- 76 top portion
- 78 bottom portion
- 80 wheel
- 82 motor
- 84 shaft

DETAILED DESCRIPTION OF THE INVENTION

The present invention provides a system and method for generating three-dimensional images of the magnetic flux leakage created within steel tendons embedded in concrete and/or grout. The method and system for creating, imaging, and analyzing the intensity of magnetic flux leakage is the subject of the present inventive method. In order to check embedded tendons for faults, the present inventive method creates a magnetic field. This magnetic field magnetizes the steel tendon. A transducer is then used to measure the magnetic field along the tendon. Images of the magnetic flux leakage show whether there is a fault, and whether the fault needs to be further investigated. Faults on the steel tendon change the magnetic flux leakage and thereby vary the magnetic field intensity. The change in magnetic field intensity is detected by the transducer, which changes the image created based on the magnetic flux leakage. This three-dimensional image is generated using a data acquisition device and a computing device connected to the transducer. The change in magnetic field intensity at the location of a fault, changes the image generated by the system, thereby indicated the existence and type of fault at that location. The details of this process and system is discussed at length in the subsequent text.

Figure 1:
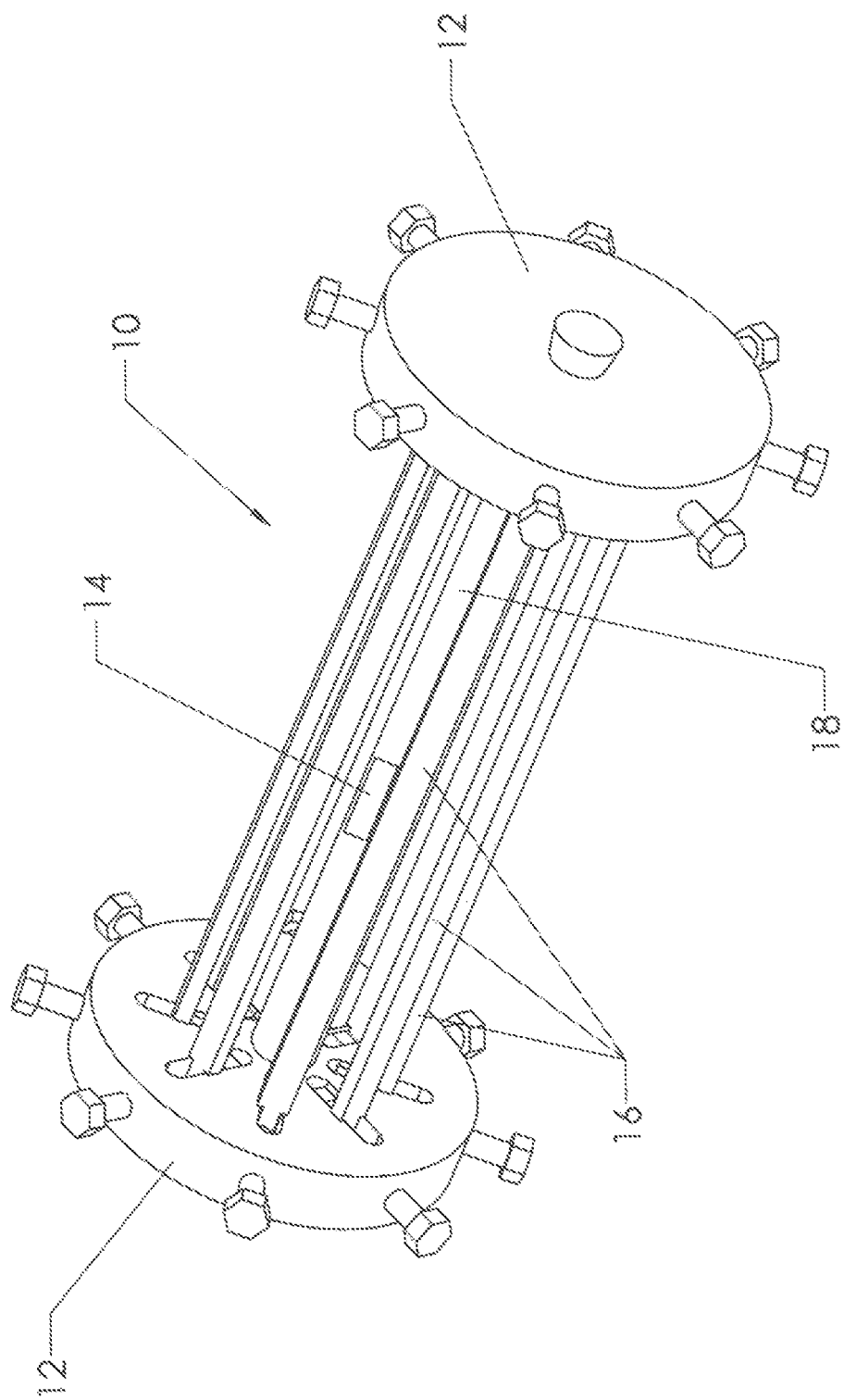
FIG. 1 is a perspective view, showing a preferred embodiment of the present invention.

FIG. 1 shows the magnetic flux leakage imaging system 10 provided in the present inventive method. Magnetic leakage flux imaging system 10 includes magnet assemblies 12, imaging array 14, mild steel bars 16 and tendon tube 18. The reader will note that imaging system 10 is not positioned around an embedded column. This is illustrated and described subsequently. While imaging system 18 is in use, the embedded tendon (including the grout, concrete or plastic) is contained within tendon tube 18. Imaging array 14 preferably encompasses at least fifty percent of the circumference of tendon tube 18 (180 degrees around the circumference of tendon tube 18). In a preferred embodiment of imaging system 10, imaging arrays 14 are positioned a full 360 degrees around the circumference of tendon tube 18. This allows the user to take readings at each angular position around the embedded tendon.

Figure 2:
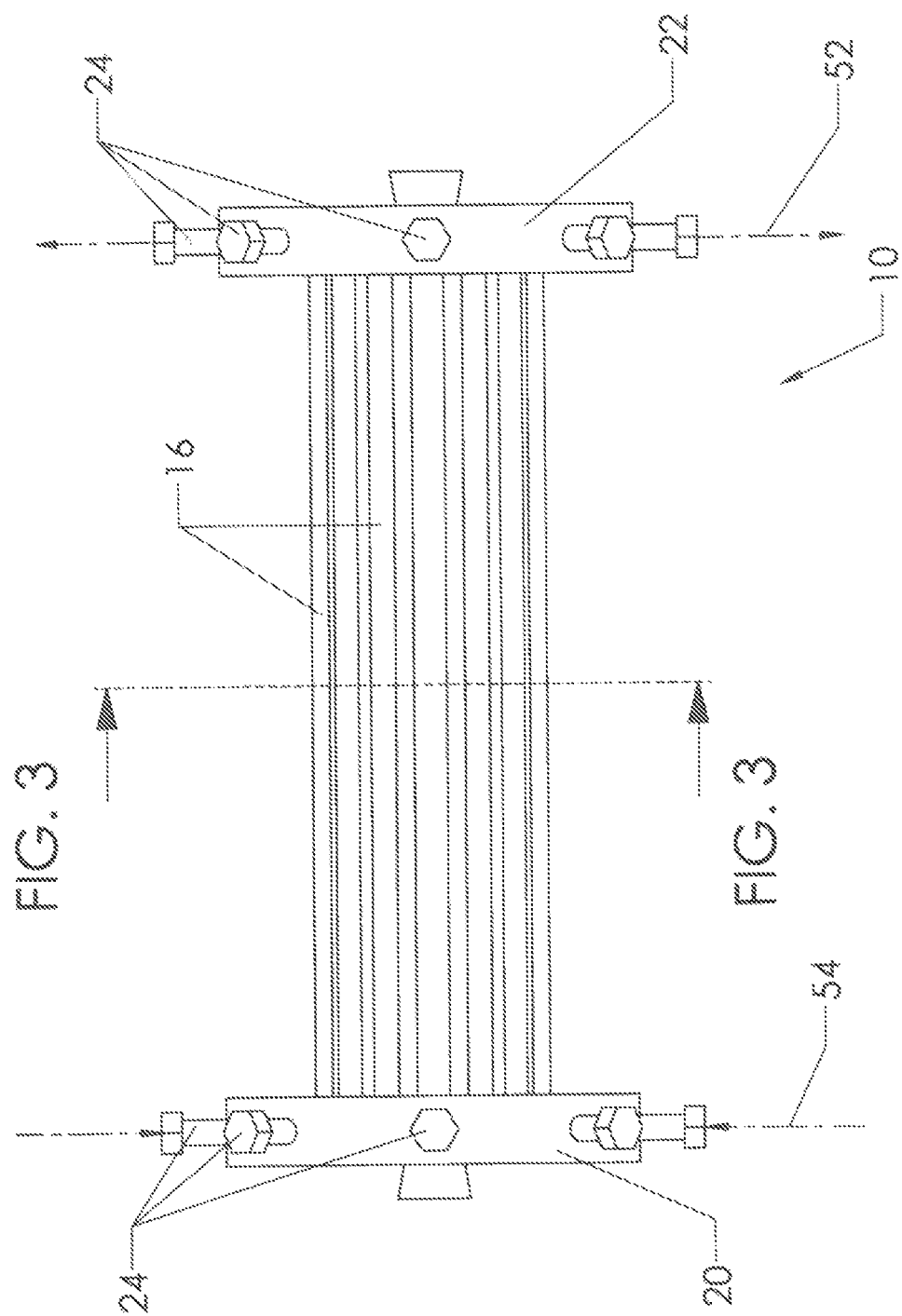
FIG. 2 is an elevation view, showing a preferred embodiment of the present invention.

FIG. 2 demonstrates several features of the present invention. First, the magnetic field created by magnetic flux leakage imaging system 10 is preferably created using two magnet assemblies. The magnet assembly on the left hand side of FIG. 2 comprises north pole magnet assembly 20. The opposite magnet assembly is the south pole magnet assembly 22 of the system. Second, mild steel bars 16 are used to connect the two magnet assemblies 12. This provides a closed loop path for magnetic flux. Third, magnet security devices 24 secure steel bar 16 to the magnets (shown in FIG. 3 and discussed subsequently) in magnet assemblies 12. Finally, the dashed line in FIG. 2 indicates the placement and direction of the sectional view in FIG. 3.

Figure 3:
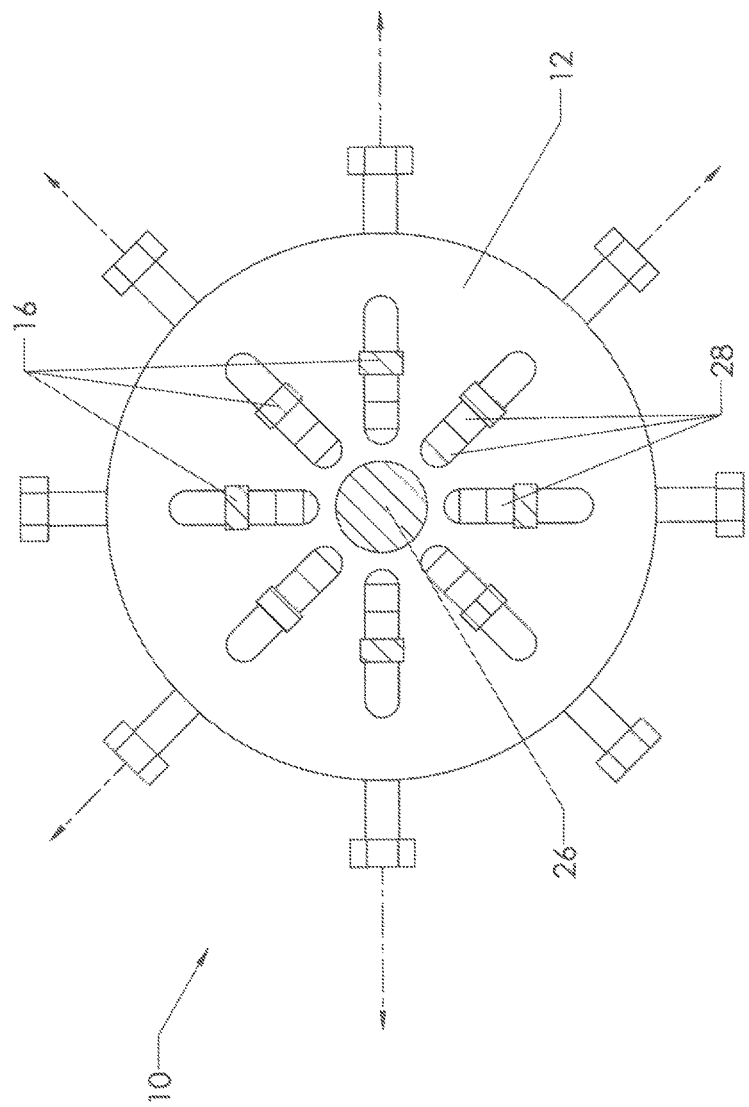
FIG. 3 is a sectional view, showing some internal features of the present invention.

As discussed briefly in the preceding text, FIG. 3 shows a sectional view of imaging system 10. The magnetic assembly is preferably arranged circumferentially around central testing cavity 26. At least two groups of magnets 28 (positioned opposite of each other) are required in order to keep the magnetic field symmetric. The current view shows eight magnet 28 groupings. In a preferred embodiment of the present invention, each magnet grouping contains at least one magnet 28, one mild steel bar 16, and one magnet security device 24. The magnet assembly 12 shown in the current view is south pole magnet assembly 22. A south pole is created by arranging magnets 28 so that the axis of magnetization is directed radially inward. Alternatively, a north pole is created by arranging the axis of magnetization of each magnet radially outward. Mild steel bars 16 create a closed loop path for magnetic flux. The reader will note that each magnet assembly 12 (the north and south poles) will look equivalent to the human eye. However, as discussed in the preceding text, the alignment of the axis of magnetization is different. The alignment of the axis of magnetization is important to the functionality of the invention despite the two poles looking identical. Referring back to FIGS. 2-3, the reader will note that the south pole magnetic axis 52 is directed outwards radially while north pole magnetic axis 54 is directed inwards radially. The arrangement of the axes creates the poles.

In a preferred embodiment of the present invention, magnets 28 are rare earth magnets. In a more preferred embodiment of the current invention, magnets 28 are neodymium-iron-boron magnets. The magnetic field created by use of such powerful magnets allows for ideal visualization of the magnetic leakage flux of the steel tendon. Although different types of magnets are discussed herein, any magnet, known or unknown can be utilized in the present invention.

Figure 4:
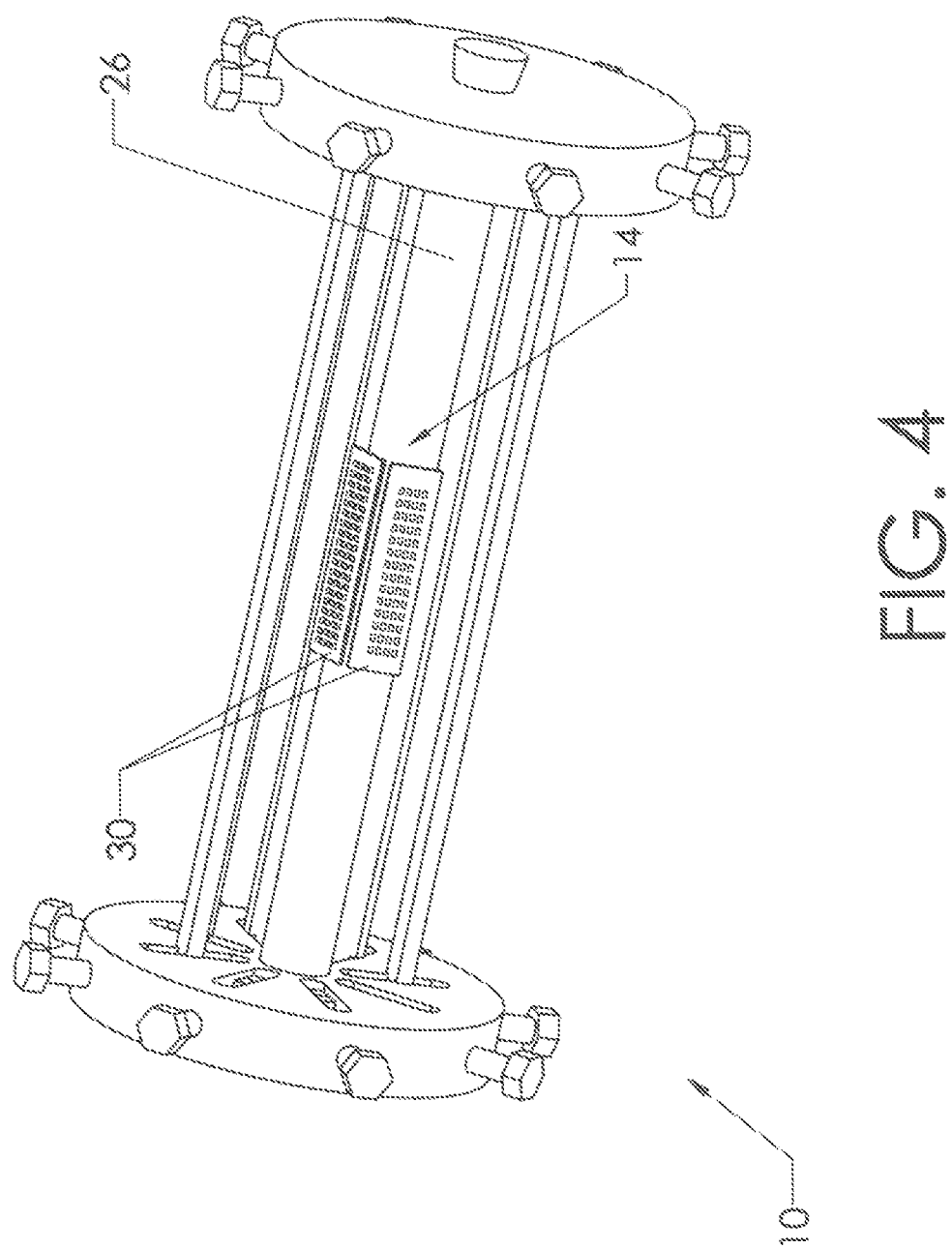
FIG. 4 is a perspective view, showing the imaging array used for the current invention.

FIG. 4 shows a perspective view of the current invention. It is important for the reader to note that three mild steel bars 16 (as illustrated in FIGS. 1 & 2) have been removed from the assembly of imaging system 10. This allows a clearer view of imaging array 14 for the reader. Imaging array 14 preferably includes at least one Hall Effect circuit board 30. Hall Effect circuit board 30 is attached to central testing cavity 26. Preferably, multiple Hall Effect circuit boards 30 are placed circumferentially around central testing cavity 26. As discussed in the preceding text, Hall Effect circuit boards 30 preferably radially span the entire circumference of testing cavity 26 in order detect the magnetic field around the full 360 degrees of the embedded tendon.

Figure 5:
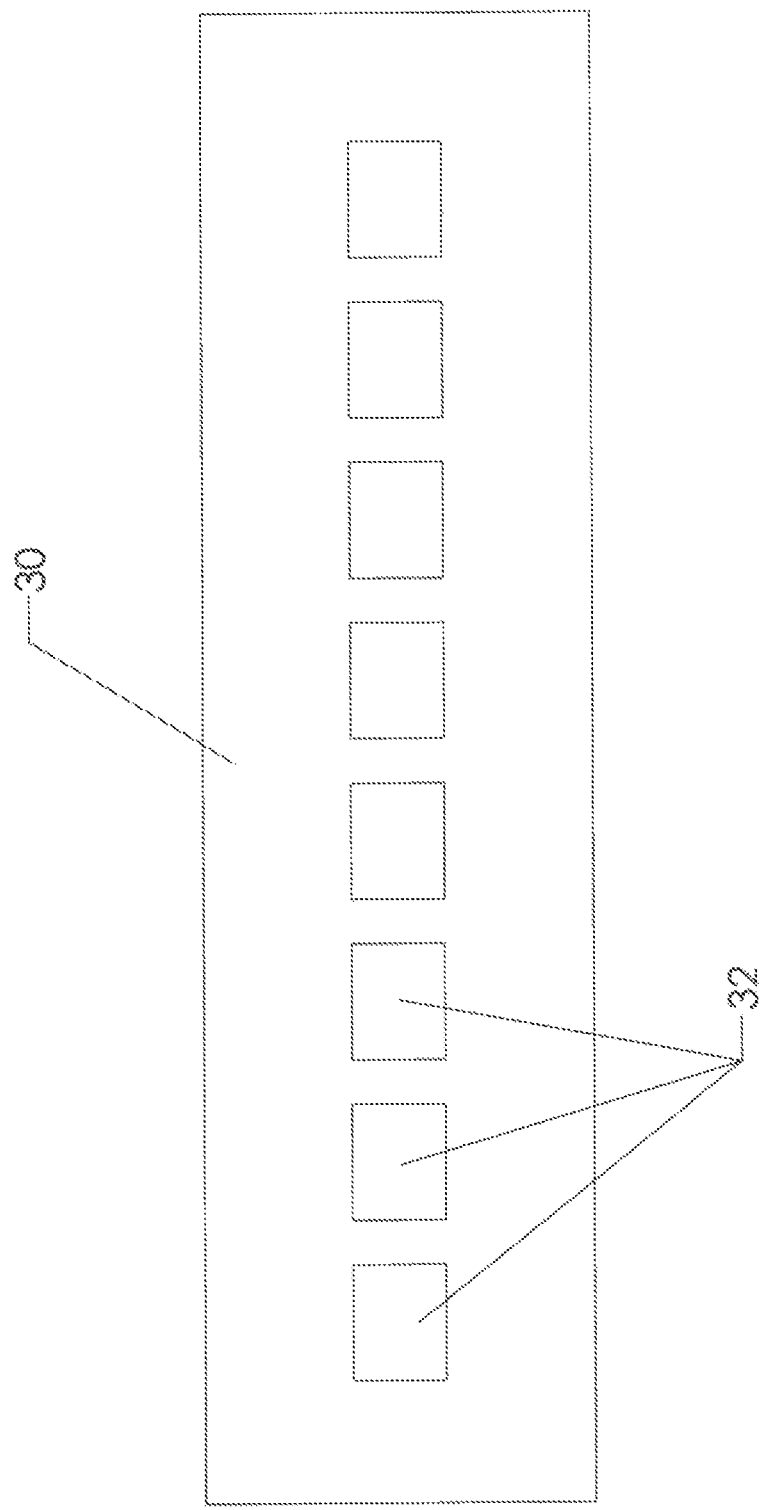
FIG. 5 is an elevation view, showing the Hall Effect sensors on the testing side of the circuit board.

In a preferred embodiment of the present invention, Hall Effect circuit board 30 includes at least one Hall Effect sensor 32 (not visible in FIG. 4). The view in FIG. 4 of circuit board 30 shows the circuitry for the Hall Effect sensors. The sensors are facing toward central testing cavity 26. FIG. 5 shows the opposite face of circuit board 30 as that shown in FIG. 4. In this view, Hall Effect sensors 32 are lined along the central axis of circuit board 30. Preferably, the sensors are equally spaced from each other in order to receive a uniform signal from the sensors. Hall Effect circuit boards 30 are positioned circumferentially around testing cavity 26 and Hall Effect sensors 32 are lined axially along testing cavity 26, which creates a grid of Hall Effect sensors radially and axially.

Figure 6:
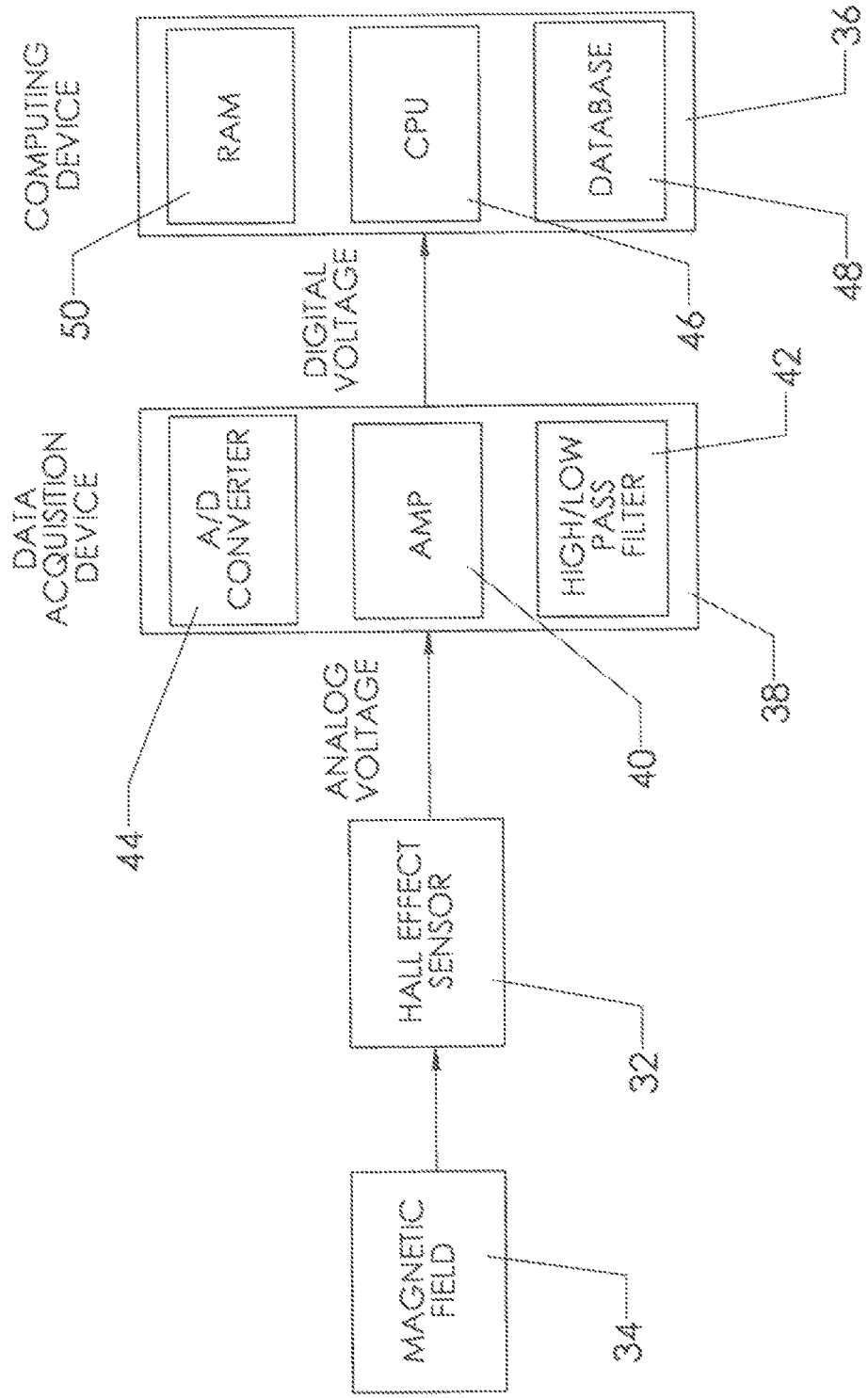
FIG. 6 is a schematic view, showing a flow chart of the current invention.

FIG. 6 shows the progression of the acquisition of data for the current invention. In the preferred embodiment of the current invention, each Hall Effect sensor 32 has the appropriate amplification and filter circuitry. Each Hall Effect sensor 32 generates a voltage proportional to the magnetic field 34 detected by the sensor. However, this signal is typically not fit to be sent straight to a computing device 36. Accordingly, the voltage from the Hall Effect sensor 32 is sent to a data acquisition device 38 via a hard-wire connection or any known method of transmitting the signal. The data acquisition device 38 performs a few tasks in order to make the signal suitable to be processed by a computing device 36—the signal may be too high or low in voltage, or the signal may be too noisy. This conditioning includes amplification or attenuation using an amplifier 40, filtering—this may be using a low pass or a high pass filter 42 (depending on the need), or isolation of the signal; and converting the signal from analog-to-digital using an Analog-to-Digital Converter 44. The data acquisition device 38 therefore produces a digital numeric value that can be provided to and manipulated by a computing device 36. This digital numeric value can be sent to the computing device 36 via any known method. In one embodiment the data acquisition device 38 is connected to the computing device 36 directly and the digital numeric value is provided to the computing device 36 via this direct connection (e.g. where data acquisition device 38 is in the form of modules connected to the computer's ports or cards connected to slots in the motherboard). Computing device 36 receives the digital numeric value from the data acquisition device 38 and manipulates the digital numeric value by using computer readable code (e.g. software) that is capable of reading the conditioned data. Computing device 36 includes a central processing unit ("CPU") 46, database 48, and random-access memory ("RAM") 50. The data acquisition software allows the user to control sampling rate, number of samples, additional filtering and amplification. In addition, the user may instruct the computing device 36 to perform other tasks that assist with the data analysis. For example, there may be a calibration for the data or it may be useful to look at the frequency or power spectrum of the signal. Whatever the desired post-processing tools may be, this allows the computing device to plot or manipulate the data in order to achieve the correct and desired analysis. In this case the post-processing manipulation of data produces an output in the form of a three-dimensional image which corresponds to the state of the tendon.

The progression discussed above is induced by means discussed in the following text. Once the invention is in position, a strong magnetic field is induced axially between the two magnetic assemblies (the north and south poles) in the tendon to be tested. The tendon under test is located in central testing cavity 26. Due to the induced magnetic field created by the two magnetic poles, any defect in the tendon being tested produces a point of flux leakage. The magnetic flux leakage created by the defect is proportional to the shape of the defect on the steel tendon. Once the magnetic flux leakage is acquired using the Hall Effect sensors, simple analysis and processing using custom software allows the user to create and image of the defect. Using this image, the user can determine the nature of the defect. In addition to determining whether the fault is manmade or corrosive, the image also indicates the type of manmade fault incurred.

Thus, by determining the type of defect, the user can determine if further inspection is necessary. Typically, manmade defects do not require further attention while corrosive defects do. This is due to the progressive nature of corrosive defects which worsen with time.

Figure 7:
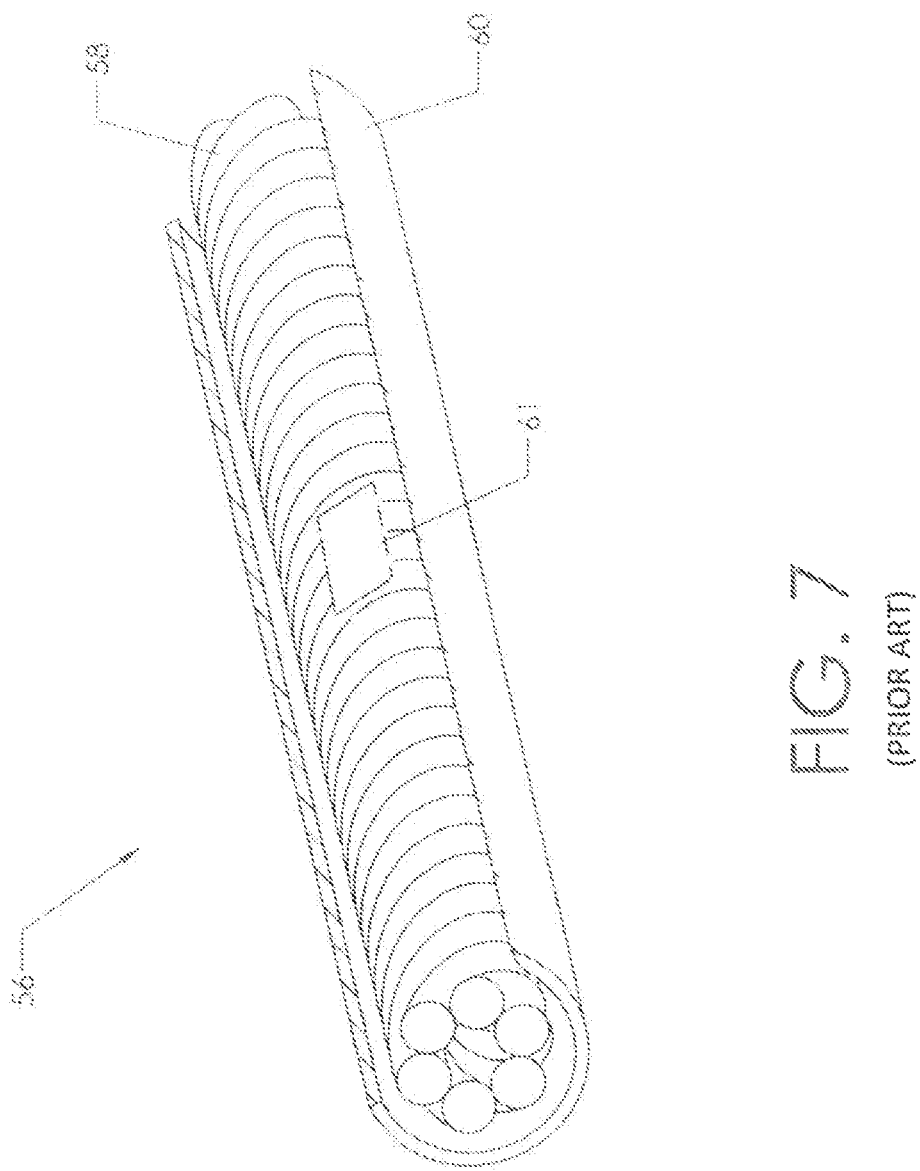
FIG. 7 is a perspective view, showing a prior art tendon.

FIG. 7 shows a cutaway view of tendon 56. Typically, tendon 56 includes twisted steel cable 58, plastic conduit 60, and grout (not shown). This particular tendon 56 excludes the grout which is typically poured to fill the space between steel cable 58 and plastic conduit 60. Of course, the present invention can be used on other columns and tendons. This particular tendon includes fault 61. Fault 61 is a cut-type fault, but can be many other faults such as corrosion, hole, etc. Once steel cable 58 is magnetized, fault 61 produces an image which is different from the image produced on a point on steel cable 58 that does not have a fault 61. Thus, the user can locate faults 61 along the tendon based on the magnetic flux leakage located at those faults.

Figure 8:
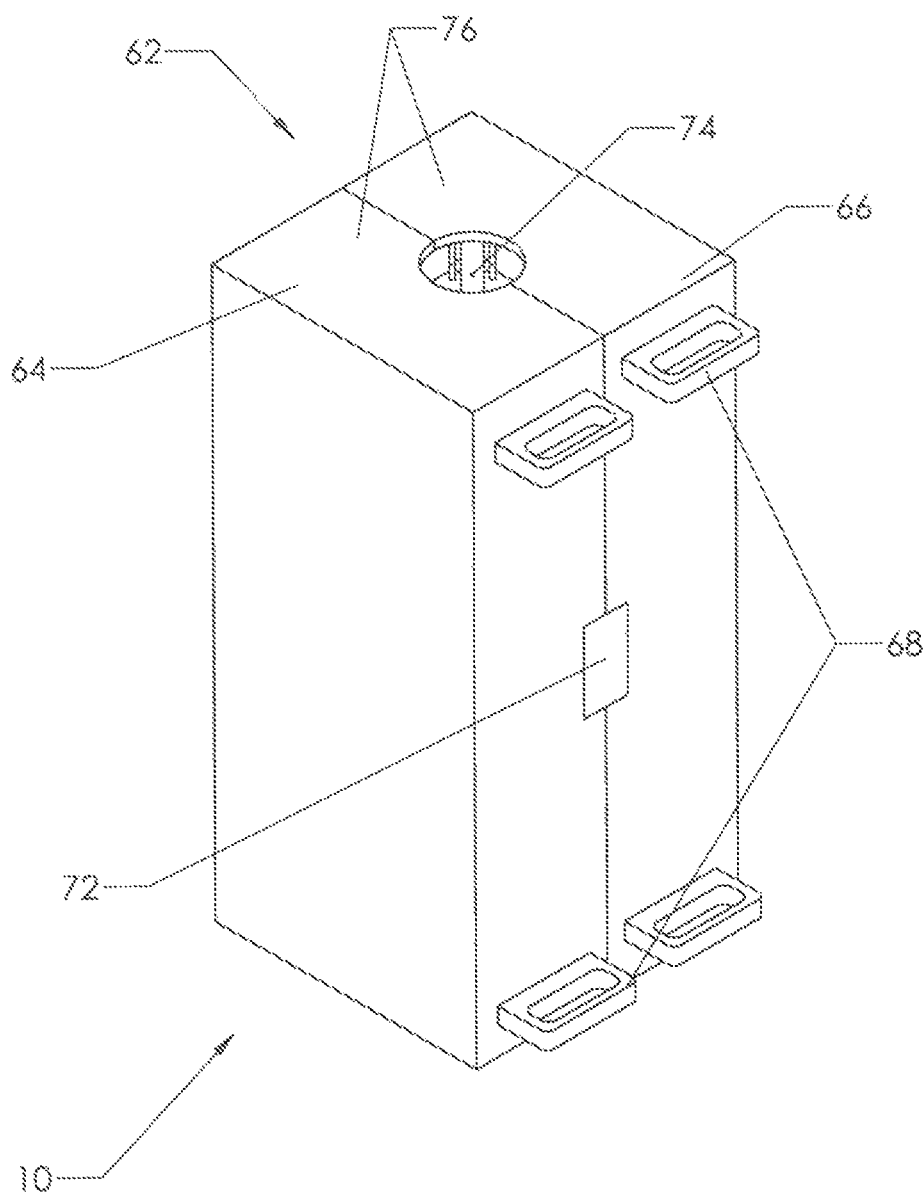
FIG. 8 is a perspective view, showing a preferred embodiment of imaging system in a closed state.
Figure 9:
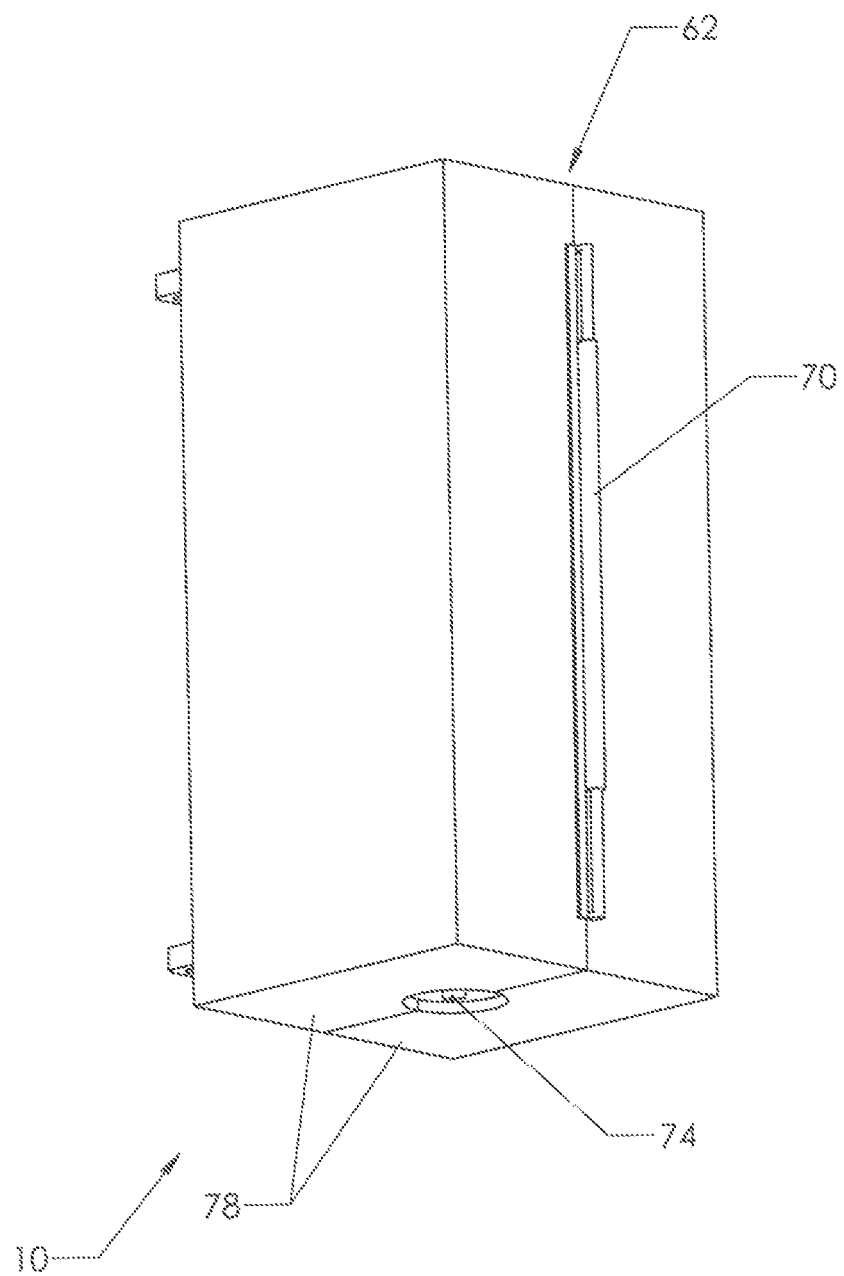
FIG. 9 is a perspective view, showing the hinge mechanism of the present invention.

FIGS. 8 and 9 shows a preferred embodiment of imaging system 10. In the present embodiment, imaging system 10 includes housing 62. Preferably, housing 62 is divided into two sections—first section 64 and second section 66. Although only two sections are described, it may be beneficial to break housing up into more than two sections. Also, while first section 64 and second section 66 are each fifty percent of housing 62, it is not necessary for each section to be exactly half. For example some embodiments may include a section which is ⅔ of the housing 62 while the other section is only ⅓.

Housing 62 preferably includes handles 68. Handles 68 are helpful when attaching imaging system 10 to tendon 56. In addition, in the manual version of the present invention (discussed further subsequently), handles 68 are used to guide imaging system 10 along tendon 56. In a preferred embodiment of the inventive method, housing 62 includes a hinge mechanism 70. Hinge mechanism 70 allows the user to easily separate first section 64 and second section 66 when attaching and removing imaging system 10 from tendon 56 while keeping the two sections attached. In order to keep first section 64 and second section 66 attached during testing, housing 62 preferably includes locking mechanism 72. Those familiar with the art will realize that instead of hinge mechanism 70 there can be a locking mechanism 72 in the place of hinge mechanism 70. In the embodiment with only locking mechanisms 72, the two separate sections, first section 64 and second section 66, are not attached at the hinge (pivot) point, and therefore must be aligned and locked into place manually. Some embodiments of the present invention may be better suited for such a design. The reader will note that hinge mechanism 70 is a simple conduit-cylinder hinge design. In this design the cylinder is located on the first section 64 of housing 62 and the conduit is located on the second section 66 of housing 62. This is simply one of many designs that are known in the art which can be used. Similarly, locking mechanism 72 can be any latch, snap, clip, or other known mechanism in the art.

Another feature illustrated in FIGS. 8 and 9 is tendon opening 74. Preferably, housing 62 includes tendon opening 74. As illustrated, tendon opening 74 is included on top portion 76 and bottom portion 78 of housing 62. This allows tendon 56 to travel through housing 62 during the imaging process.

Figure 10:
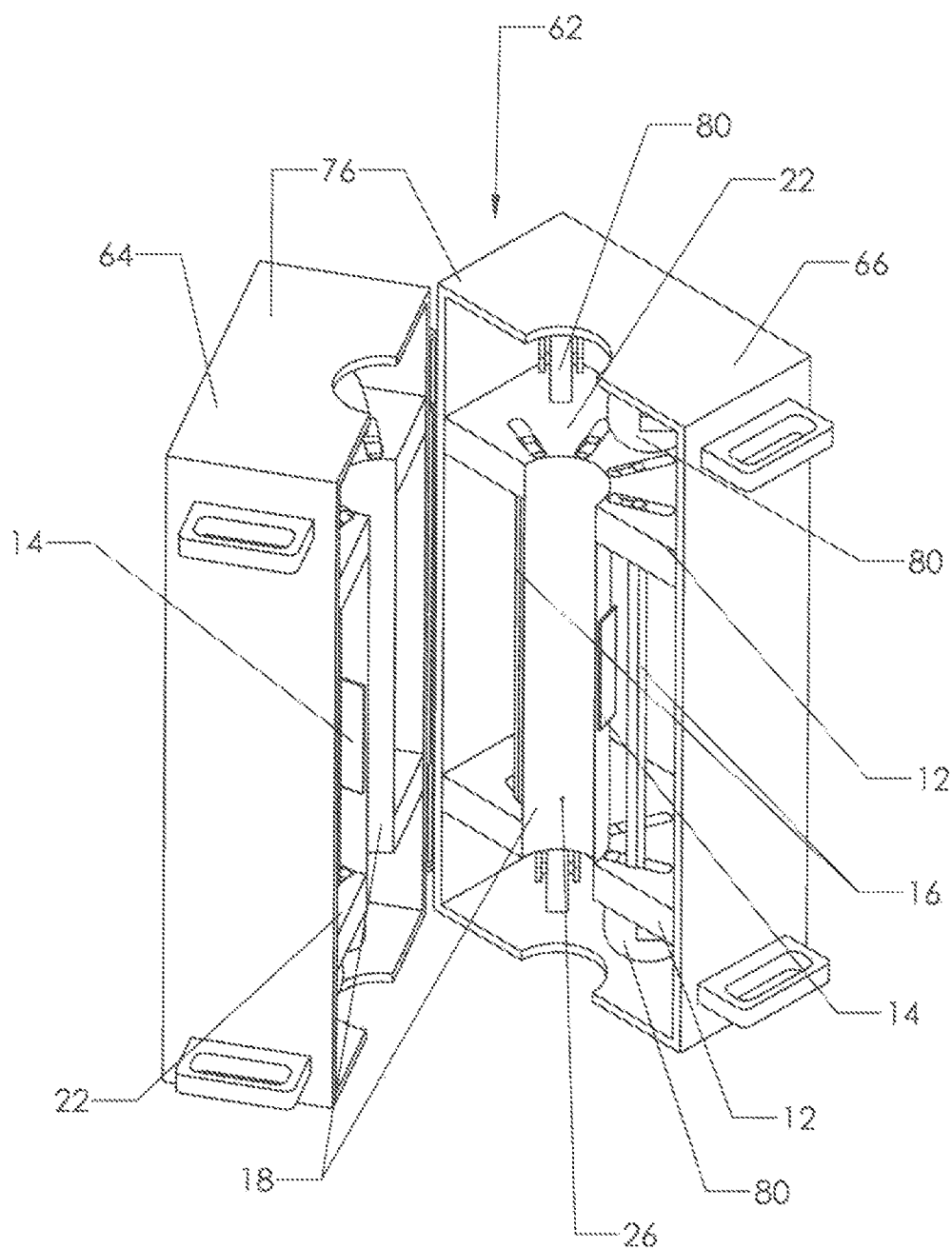
FIG. 10 is a perspective view, showing the present invention in an open state.

FIG. 10 shows a preferred embodiment of the present invention in an "open" state. As illustrated, first section 64 and second section 66 on housing 62 have been separated using hinge mechanism 70 as a pivot point. In this view, the inside of housing 62 is visible. The reader will note that the components shown in FIG. 10 are very similar to the components of FIG. 1. Magnetic flux leakage imaging system includes magnet assemblies 12, imaging arrays 14, mild steel bars 16, and tendon tube 18. In this embodiment, tendon tube 18 also acts as central testing cavity 26, which is a cylindrical cavity for which tendon 56 fits. Each component functions identically to those in the previous embodiment. The reader will note, however, that the components are divided into two sections as opposed to one solid piece as in the previous embodiment. Similarly, imaging array 10 includes south pole assembly 22 and north pole assembly 20. In addition to all the necessary components used to produce three dimensional images of the magnetic flux leakage of the tendon, the embodiment of FIG. 10 includes a method of traveling along tendon 56. Preferably, the inside of housing 62 includes at least four wheels 80. In a preferred embodiment of the present invention, there are four pairs of wheels, as illustrated. As shown, the top portion 76 of second section 66 preferably includes a pair of wheels 80 and the bottom portion 78 of second section 66 preferably includes a pair of wheels 80. Although not visible in FIG. 10, the same configuration is used for first section 64.

Figure 11:
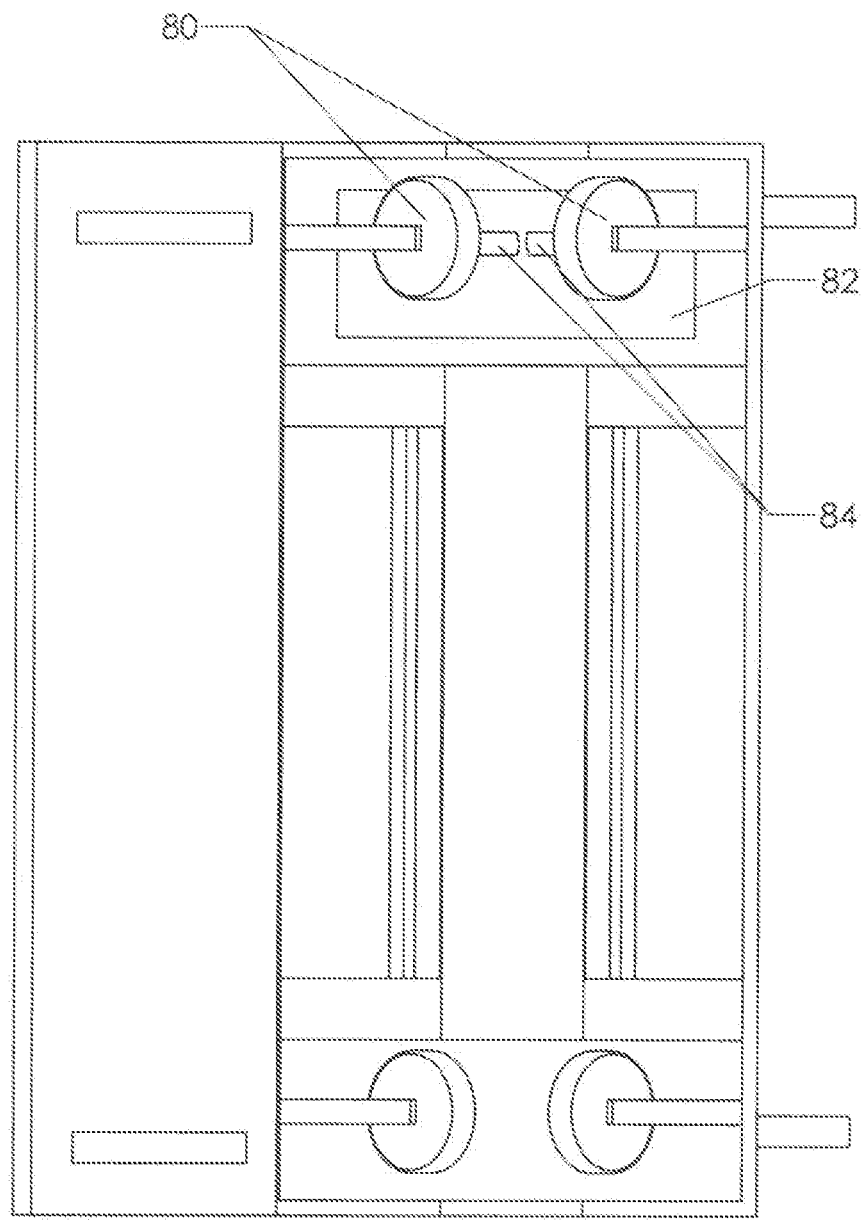
FIG. 11 is an elevation view, showing a motorized version of the present invention.

FIG. 11 shows an elevation view of imaging system 10. In this embodiment of imaging system 10, the method of traveling along tendon 56 is motorized. In this embodiment, housing 62 preferably includes motor 82. Preferably motor 82 is a dual shaft motor. Of course, motor 82 can be broken up into two, single shaft motors if desired. Each shaft 84 is connected to the axles of wheels 80, as shown. As the motor shafts 84 rotate, imaging system 10 travels along tendon 56. The reader will note that only a single motor is shown. In some instances, a motor may be required for each pair of wheels 80, only two pairs of wheels 80, or for only one pair of wheels 80. This is largely dependent on the power of the motor 82, the weight of imaging system 10, and the stability of the entire system including the tendon 56. Preferably, the user can control motor 82 remotely. Because imaging system 10 provides images of the magnetic flux leakage in real time, it may be desirable to reverse or stop in a certain position on tendon 56 during testing. In some instances, it may be desirable for the motor to run continuously while keeping track of the position of the motor on the tendon. In this case analysis of the images could be accomplished after testing without losing the position on the tendon where there is need for more analysis.

In another embodiment of the present invention, imaging system 10 does not include a motor 82. In this instance, the user simple grasps handle 68 and pulls housing 62 along tendon 56. In addition, a temporary track can be attached to tendon 56 which allows a corresponding slider or wheel attached to housing 62 to engage that track. Those familiar with the art will realize that there are multiple translating systems which can be used to move imaging system 10 along tendon 56.

Figure 12:
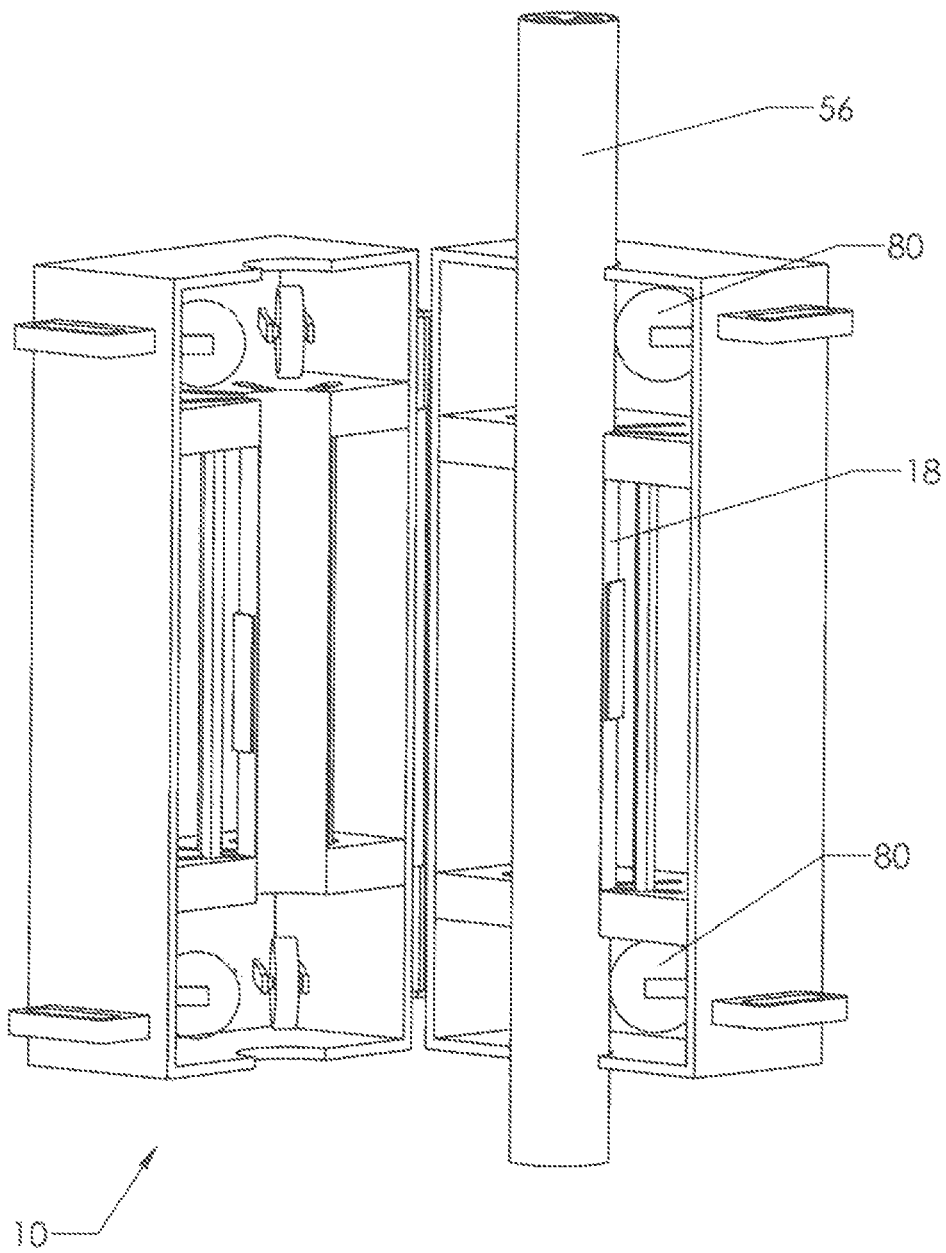
FIG. 12 is a perspective view, showing the present invention in the process of being attached to a tendon.
Figure 13:
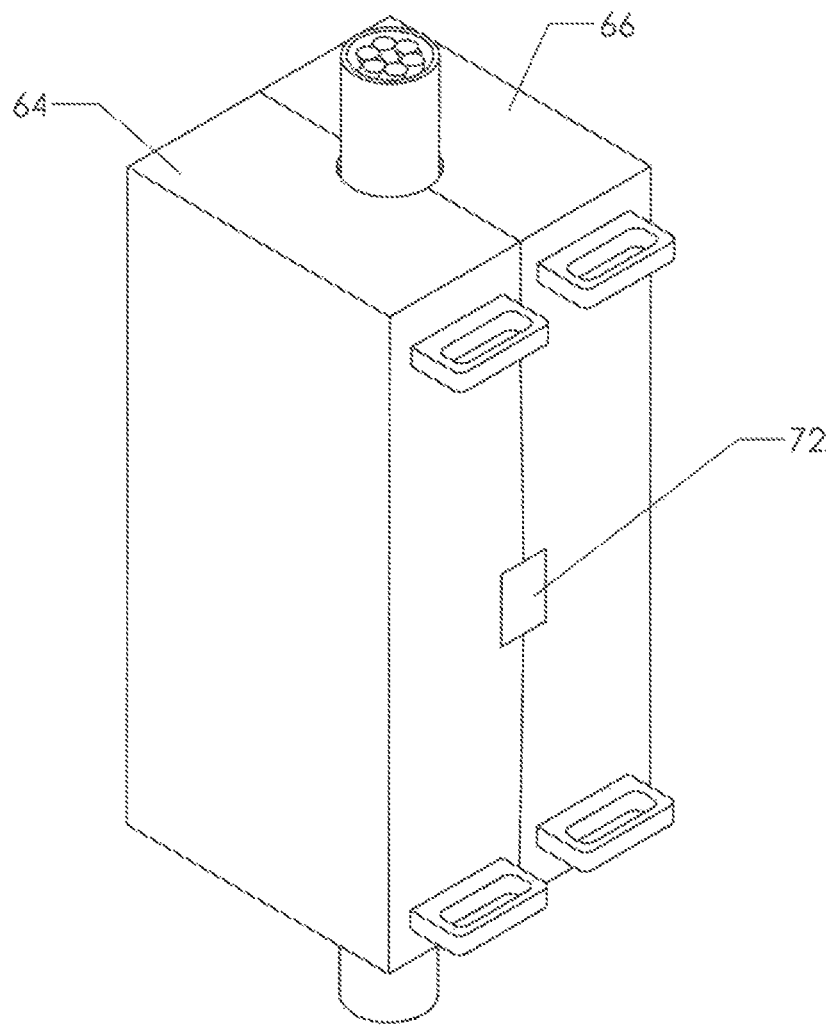
FIG. 13 is a perspective view, showing the present invention as it translates along a tendon.

FIG. 12 shows imaging system 10 as it is being mounted to tendon 56. Preferably, wheels 80 contact tendon 56 such that tendon tube 18 does not contact tendon 56. This allows imaging system 10 to travel along tendon 56. Preferably the only contact between imaging system 10 and tendon 56 are wheels 80. Once tendon 56 is aligned with wheels 80, the user joins first section 64 and second section 66. This is shown in FIG. 13. Locking mechanism 72 prevents first section 64 and second section 66 from separating.

After imaging system 10 is attached to tendon 56, the user can begin acquiring data. Since magnets 28 and mild steel bars 16 are already in place once the imaging system 10 is attached, the tendon 56 is already magnetized. Thus, in order to begin acquiring data and acquiring images, the user needs only to power the Hall Effect circuit boards 30, the data acquisition device 38, and the computing device 36. Then, the user can either manually translate imaging device 10 along tendon 56 or activate motor 82.

As imaging device 10 travels along tendon 56, the section of twisted steel cable 58 within tendon 56 becomes magnetized between the north pole assembly 20 and south pole assembly 22 of imaging device 10. In the case where there is no fault, Hall Effect sensors 32 detect just a typical magnetic field created by two poles with a steel bar between them. This magnetic field intensity is converted into voltage and condition as described in the preceding text. Base on the magnetic field, a three dimensional image is generated. However, in the case where there is a fault 61 on tendon 56 (on the steel cable 58 portion of tendon 56) the magnetic field is not uniform, which creates a magnetic flux leakage. This magnetic flux leakage is detected by the Hall Effect sensors and since there is a flux in the field, the image generated due to the presence of the flux is different from the image generated when there is a constant magnetic field. Furthermore, the flux created by a cut or nick is different from the flux created by corrosion. Thus, the image generated due to a nick or cut, which is not progressive and does not need to be further investigated, is different from the image generated by corrosion, which requires further investigation. This method of investigating faults present on a tendon is non-destructive and non-intrusive. Other methods are either destructive or are extremely complex and require complicated calculations and post-processing. The present inventive method uses a simple data acquisition device and program to generate images related to a fault and the source of the fault.

The preceding description contains significant detail regarding the novel aspects of the present invention. It should not be construed, however, as limiting the scope of Having described my invention, I claim:

1. A method for generating a series of three-dimensional images of a magnetic flux leakage created by a fault on a steel tendon embedded in concrete, wherein said steel tendon has a length, comprising the steps of:
   a. providing a magnetic flux leakage imaging system, including,
      i. a north pole magnet assembly,
      ii. a south pole magnet assembly opposite said north pole magnet assembly,
      iii. a cylindrical, central testing cavity spanning the distance between said north pole magnet assembly and said south pole magnet assembly, having a first end proximate said north pole magnet assembly, a second end proximate said south pole magnet assembly, and a midpoint,
      iv. a series of magnets arranged radially around said first end of said central testing cavity within said north pole magnet assembly arranged such that a north magnetic pole is created,
      v. a series of magnets arranged radially around said second end of said central testing cavity within said south pole magnet assembly arranged such that a south magnetic pole is created,
      vi. an imaging array, including a series of transducers, arranged radially around said central testing cavity, proximate said midpoint of said central testing cavity,
      vii. a series of bars arranged radially around said central testing cavity, each having a first end and a second end, where said first end engages said north pole magnet assembly and said second end engages said south pole magnet assembly;
   b. providing a translation system attached to said magnetic flux imaging system, wherein said translation system is capable of engaging and translating along said tendon;
   c. aligning said magnetic flux leakage imaging system such that said central testing cavity surrounds and said magnetic assemblies surround said tendon, thereby inducing a magnetic field;
   d. engaging said tendon with said translation system;
   e. translating said imaging system along said length of said tendon using said translation system;
   f. detecting said magnetic flux leakage produced by said magnetic field on said tendon, at a series of points along said length of said tendon, by said magnetic assemblies using said imaging array;
   g. acquiring a voltage proportional to said magnetic flux leakage produced by said tendon at said points along said length of said tendon using a data acquisition device;
   h. processing said voltage using a computing device;
   i. generating said series of three-dimensional images of said magnetic flux leakage using said computing device as said translation system translates along said length of said tendon; and
   j. analyzing said series of three-dimensional images in order to determine if a point along said length of said tendon contains a fault.

2. The method for generating a series of three-dimensional images as recited in claim 1, wherein said magnetic flux imaging system further comprises:
   a. a housing, having a top portion, a bottom portion, and an outer surface;
   b. wherein said north pole magnet assembly is connected to said top portion;
   c. wherein said south pole magnet assembly is connected to said bottom portion; and
   d. wherein said housing is vertically divided into a first section and a second section.

3. The method for generating a series of three-dimensional images as recited in claim 1, wherein said series of transducers on said imaging array are Hall Effect sensors.

4. The method for generating a series of three-dimensional images as recited in claim 1, wherein said magnets are arranged such that there are eight evenly spaced groups of magnets arranged radially.

5. The method for generating a series of three-dimensional images as recited in claim 4, wherein said magnets are neodymium-iron-boron magnets.

6. The method for generating a series of three-dimensional images as recited in claim 2, wherein said outer surface of said housing includes at least one handle located on each section of said housing.

7. The method for generating a series of three-dimensional images as recited in claim 2, wherein said housing includes a hinge mechanism.

8. The method for generating a series of three-dimensional images as recited in claim 7, wherein:
   a. said first section of said housing includes a cylindrical part;
   b. said second section of said housing includes a conduit part; and
   c. said cylindrical part engages said conduit part in order to create a hinge mechanism.

9. The method for generating a series of three-dimensional images as recited in claim 1, wherein said translation system further comprises:
   a. at least four pairs of wheels;
   b. wherein each wheel engages said tendon;
   c. wherein at least two pairs of wheels are proximate said north pole magnet assembly and opposite each other; and
   d. wherein at least two pairs of wheels are proximate said south pole magnet assembly and opposite each other.

10. The method for generating a series of three-dimensional images as recited in claim 9, wherein at least one pair of wheels are motorized.

11. A method for generating a series of three-dimensional images of a magnetic flux leakage created by a fault on a steel tendon embedded in concrete, wherein said steel tendon has a length, comprising the steps of:
    a. providing a magnetic flux leakage imaging system, including,
       i. a north pole magnet assembly,
       ii. a south pole magnet assembly opposite said north pole magnet assembly,
       iii. a cylindrical, central testing cavity spanning the distance between said north pole magnet assembly and said south pole magnet assembly, having a first end proximate said north pole magnet assembly, a second end proximate said south pole magnet assembly, and a midpoint,
       iv. a series of magnets arranged radially around said first end of said central testing cavity within said north pole magnet assembly arranged such that a north magnetic pole is created,
       v. a series of magnets arranged radially around said second end of said central testing cavity within said south pole magnet assembly arranged such that a south magnetic pole is created,
vi. an imaging array, including a series of Hall Effect transducers, arranged radially around said central testing cavity, proximate said midpoint of said central testing cavity,
vii. a series of bars arranged radially around said central testing cavity, each having a first end and a second end, where said first end engages said north pole magnet assembly and said second end engages said south pole magnet assembly,
viii. wherein said magnetic flux leakage imaging system is capable of separating such that said imaging system surrounds said tendon;
b. providing a translation system attached to said magnetic flux imaging system, wherein said translation system is capable of engaging and translating along said tendon;
c. aligning said magnetic flux leakage imaging system such that said central testing cavity surrounds and said magnetic assemblies surround said tendon, thereby inducing a magnetic field;
d. engaging said tendon with said translation system;
e. translating said imaging system along said length of said tendon using said translation system;
f. detecting said magnetic flux leakage produced by said magnetic field on said tendon, at a series of points along said length of said tendon, by said magnetic assemblies using said imaging array;
g. acquiring a voltage proportional to said magnetic flux leakage produced by said tendon at said points along said length of said tendon using a data acquisition device;
h. processing said voltage using a computing device;
i. generating said series of three-dimensional images of said magnetic flux leakage using said computing device as said translation system translates along said length of said tendon; and
j. analyzing said series of three-dimensional images in order to determine if a point along said length of said tendon contains a fault.

12. The method for generating a series of three-dimensional images as recited in claim 11, wherein said magnetic flux imaging system further comprises:
a. a housing, having a top portion, a bottom portion, and an outer surface;
b. wherein said north pole magnet assembly is connected to said top portion; and
c. wherein said south pole magnet assembly is connected to said bottom portion.

13. The method for generating a series of three-dimensional images as recited in claim 12, wherein said housing is capable of separating such that said housing surrounds said tendon.

14. The method for generating a series of three-dimensional images as recited in claim 11, wherein said magnets are arranged such that there are eight evenly spaced groups of magnets arranged radially.

15. The method for generating a series of three-dimensional images as recited in claim 14, wherein said magnets are neodymium-iron-boron magnets.

16. The method for generating a series of three-dimensional images as recited in claim 12, wherein said outer surface of said housing includes at least one handle located on each section of said housing.

17. The method for generating a series of three-dimensional images as recited in claim 12, wherein said housing includes a hinge mechanism.

18. The method for generating a series of three-dimensional images as recited in claim 17, wherein:
a. said first section of said housing includes a cylindrical part;
b. said second section of said housing includes a conduit part; and
c. said cylindrical part engages said conduit part in order to create a hinge mechanism.

19. The method for generating a series of three-dimensional images as recited in claim 11, wherein said translation system further comprises:
a. at least four pairs of wheels;
b. wherein each wheel engages said tendon;
c. wherein at least two pairs of wheels are proximate said north pole magnet assembly and opposite each other; and
d. wherein at least two pairs of wheels are proximate said south pole magnet assembly and opposite each other.

20. The method for generating a series of three-dimensional images as recited in claim 19, wherein at least one pair of wheels are motorized.

* * * * *